US012642507B2

(12) United States Patent
Kim

(10) Patent No.: US 12,642,507 B2
(45) Date of Patent: Jun. 2, 2026

(54) ENHANCED SEQUENTIAL IMAGE DATA GENERATION TECHNIQUES

(71) Applicant: GE Precision Healthcare LLC, Wauwatosa, WI (US)

(72) Inventor: Jeong Seok Kim, Seongnam-si (KR)

(73) Assignee: GE Precision Healthcare LLC

( * ) Notice: Subject to any disclaimer, the term of this patent is extended or adjusted under 35 U.S.C. 154(b) by 254 days.

(21) Appl. No.: 18/389,170

(22) Filed: Nov. 13, 2023

(65) Prior Publication Data

US 2025/0152141 A1 May 15, 2025

(51) Int. Cl.
*A61B 8/00* (2006.01)
(52) U.S. Cl.
CPC .................................... *A61B 8/488* (2013.01)
(58) Field of Classification Search
CPC .................................................... A61B 8/488
See application file for complete search history.

(56) References Cited

U.S. PATENT DOCUMENTS

| | | | |
|---|---|---|---|
| 8,206,302 B2 | 6/2012 | Zhang | |
| 2009/0012398 A1* | 1/2009 | Zhang | G01S 7/52077 600/453 |
| 2020/0405269 A1* | 12/2020 | Swisher | G06N 3/08 |
| 2023/0228873 A1* | 7/2023 | Apostolakis | A61B 8/085 73/641 |

OTHER PUBLICATIONS

Sun et al.; Research on obtaining pseudo CT images based on stacked generative adversarial network; Quant Imaging Med Surg. May 2021;11(5):1983-2000. (Year: 2021).*

* cited by examiner

*Primary Examiner* — Chao Sheng
(74) *Attorney, Agent, or Firm* — MCANDREWS HELD & MALLOY, LTD; Daniel Bissing; David Bates

(57) ABSTRACT

A method for enhancing sequential ultrasound image data in an ultrasound system includes: acquiring, by an ultrasound probe of the ultrasound system, first image data during a first period of time and third image data during a third period of time subsequent to the first period of time; and inferring inferred image data corresponding to a second period of time, wherein the second period of time is intermediate the first period of time and the third period of time, wherein the inferred image data is inferred by: inputting, into a trained machine-learning model, degraded image data; and generating, by the trained machine-learning model, the inferred image data.

17 Claims, 6 Drawing Sheets

610 Receive at trained model incomplete sequential image data

620 Generate degraded image data for incomplete sections of image sequence data

630 Generate, by trained model, enhanced image sequence data

600

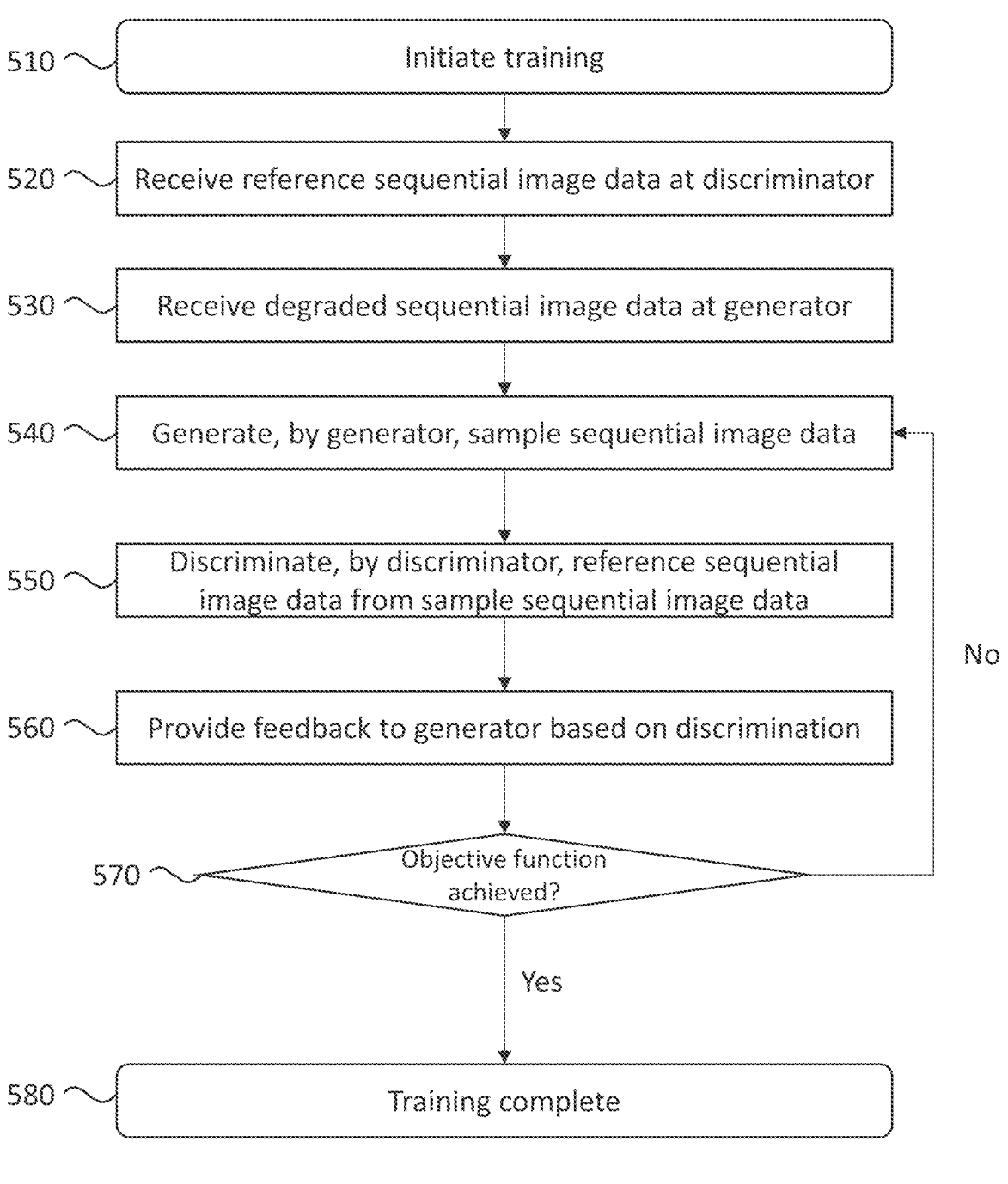

510 — Initiate training

520 — Receive reference sequential image data at discriminator

530 — Receive degraded sequential image data at generator

540 — Generate, by generator, sample sequential image data

550 — Discriminate, by discriminator, reference sequential image data from sample sequential image data 560 — Provide feedback to generator based on discrimination 570 — Objective function achieved?

No

Yes

580 — Training complete

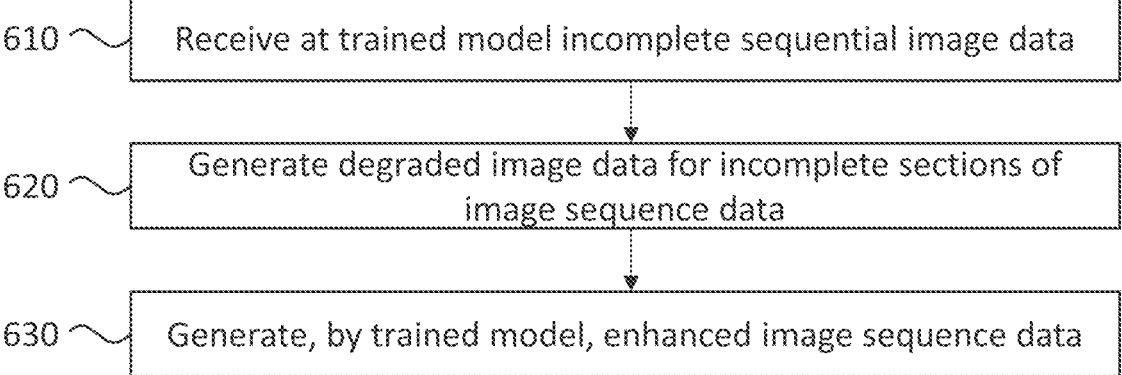
610 — Receive at trained model incomplete sequential image data
620 — Generate degraded image data for incomplete sections of image sequence data
630 — Generate, by trained model, enhanced image sequence data
600
FIG. 6

ENHANCED SEQUENTIAL IMAGE DATA GENERATION TECHNIQUES

FIELD

Certain embodiments relate to ultrasound imaging. More specifically, certain embodiments relate to techniques for enhancing Doppler imaging of time-sequence processes, such as blood-flow imaging.

BACKGROUND

Ultrasound imaging is a medical imaging technique for imaging human anatomy. Ultrasound imaging may be used to image or analyze blood flow through a patient's cardio-vascular system. Ultrasound imaging uses real time, non-invasive high frequency sound waves to produce two-dimensional (2D), three-dimensional (3D), and/or four-dimensional (4D) (i.e., real-time/continuous 3D image data) image data.

Certain ultrasound imaging systems may include the ability to image using multiple modes, such as B-mode, Doppler mode, and/or color Doppler mode. According to some techniques, an ultrasound imaging system may sequentially implement different techniques over a time span. For example, the ultrasound imaging system may obtain B-mode image data at a first time, Doppler image data at a second, subsequent time, B-mode image data at a third, subsequent time, Doppler image data at a fourth, subsequent time, etc. In this example, Doppler image data is not obtained in the first and third times. If a patient's blood flow is being imaged, then there is missing data, as the patient's blood is constantly moving, and is not in the same distribution at each of the four times. Each of these "times" may refer to a substantially instantaneous period of time and/or an extended period of time. A given extended period of time may include multiple timeslots or frames, which includes corresponding multiple, sequential image data. These "times" may be of equal or varying duration.

Further limitations and disadvantages of conventional and traditional approaches will become apparent to one of skill in the art, through comparison of such systems with some aspects of the present disclosure as set forth in the remainder of the present application with reference to the drawings.

SUMMARY

According to embodiments, a method for enhancing sequential ultrasound image data in an ultrasound system includes: acquiring by an ultrasound probe of the ultrasound system, first image data during a first period of time and third image data during a third period of time subsequent to the first period of time; and inferring inferred image data corresponding to a second period of time, wherein the second period of time is intermediate the first period of time and the third period of time, wherein the inferred image data is inferred by: inputting, into a trained machine-learning model, degraded image data; and generating, by the trained machine-learning model, the inferred image data. The first image data, the third image data, the inferred image data may include Doppler image data. The degraded image data may be obtained by mixing noise with the first image data. The inferred image data may include time domain data. The inferred Doppler image data may include frequency domain data. The trained machine-learning trained model may include a generative adversarial network (GAN) model. The GAN model may include a generator and a discriminator, and may be trained by: inputting the degraded image data into the generator; outputting, by the generator, samples corresponding to the degraded image data to the discriminator; inputting reference image data into the discriminator; and discriminating with the discriminator between the degraded image data and the reference image data with the discriminator according to at least one function. The samples may include a probability density function of real samples of the degraded image data. The step of discriminating with the discriminator may include minimizing a loss function. The reference image data may be obtained from imaging of a phantom device. The empirical training Doppler image data may be obtained from Doppler imaging of a human. The degraded image data may be generated by mixing noise with the first image data. The method may further include acquiring B-mode data during the second period of time.

According to embodiments, a system for enhancing sequential ultrasound image data includes: an ultrasound probe configured to obtain first image data during a first period of time and third image data during a third period of time subsequent to the first period of time; and a processor configured to infer inferred image data corresponding to a second period of time, wherein the second period of time is intermediate the first period of time and the third period of time, wherein the inferred image data is inferred by: inputting, into a trained machine-learning model, degraded image data; and generating, by the trained machine-learning model, the inferred image data. The first image data, the third image data, the inferred image data may include Doppler image data. The processor may be further configured to generate the degraded image data by mixing noise with the first image data. The trained machine-learning trained model may include a generative adversarial network (GAN) model. The processor may be further configured to implement the GAN model using a generator and a discriminator, and wherein the processor is further configured to train the GAN model by: inputting the degraded image data into the generator; outputting, by the generator, samples corresponding to the degraded image data to the discriminator; inputting reference image data into the discriminator; and discriminating with the discriminator between the degraded image data and the reference image data with the discriminator according to at least one function. The degraded image data may be generated by mixing noise with the first image data. The ultrasound probe may be further configured to acquire B-mode data during the second period of time.

These and other advantages, aspects and novel features of the present disclosure, as well as details of an illustrated embodiment thereof, will be more fully understood from the following description and drawings.

BRIEF DESCRIPTION OF SEVERAL VIEWS OF THE DRAWINGS

FIG. 5 is a flow chart illustrating exemplary steps that may be utilized for training a machine learning model for enhancing sequential ultrasound image data, in accordance with various embodiments.

FIG. 6 is a flow chart illustrating exemplary steps that may be utilized for using a machine learning model to enhance ultrasonic image sequence data, in accordance with various embodiments.

DETAILED DESCRIPTION

Figure 1:
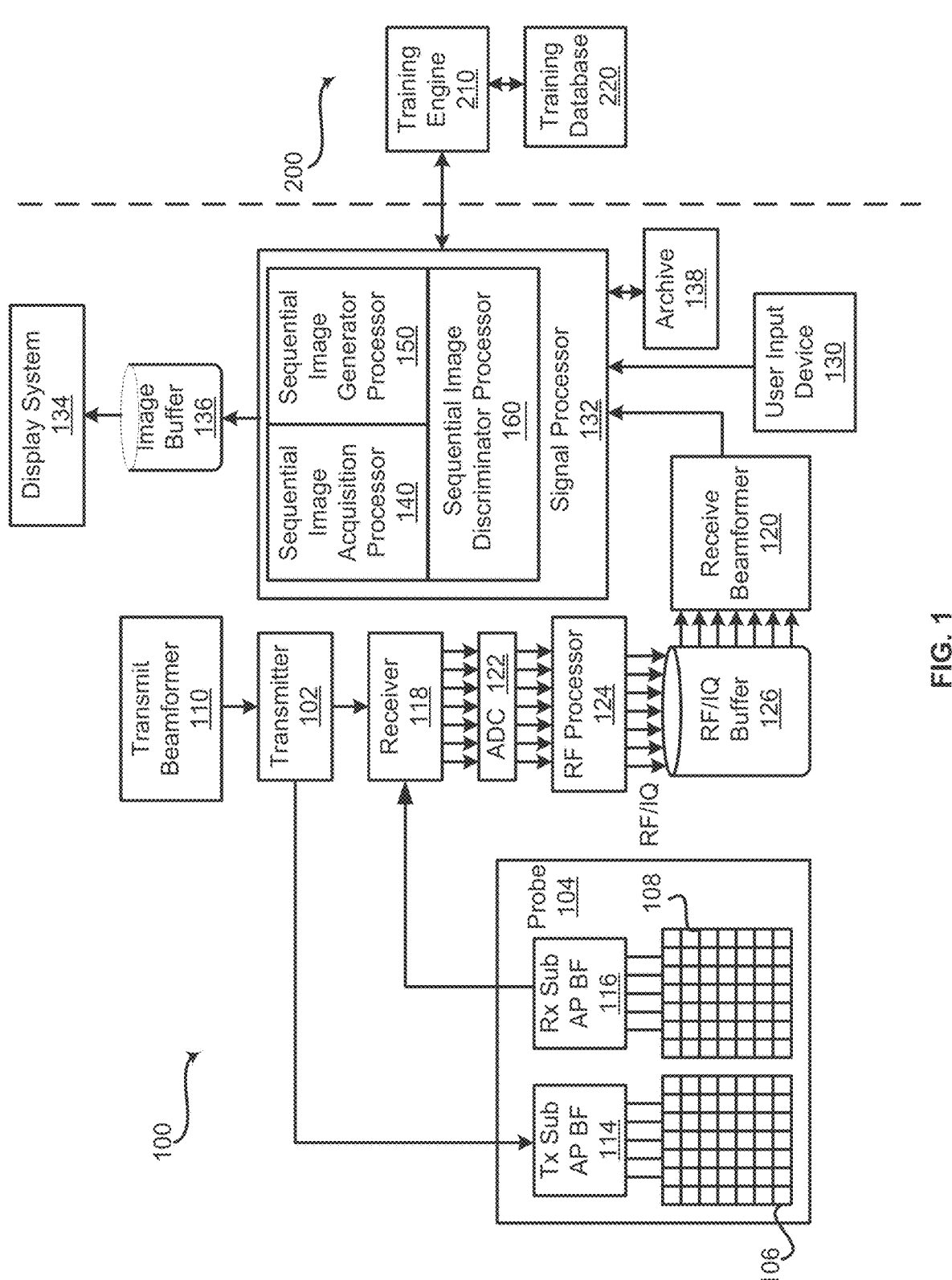
FIG. 1 is a block diagram of an exemplary ultrasound system that is operable for enhancing sequential ultrasound image data using a machine learning model, in accordance with various embodiments.

Certain embodiments may be found in a method and system for enhancing time-sequence ultrasonic imaging, such as blood-flow imaging, using machine learning. Aspects of the present disclosure have the technical effect of enhancing time-sequence imaging using machine learning in order to help provide a diagnosis. Various embodiments have the technical effect of processing acquired ultrasound image data to enhance time-sequence ultrasound image data using machine learning. Certain embodiments have the technical effect of predicting image data from a given period of time when no ultrasonic image data was obtained at that time. Certain embodiments have the technical effect of predicting ultrasonic image data (e.g., Doppler image data) from a given period of time when no ultrasonic image data was obtained at that time. Aspects of the present disclosure have the technical effect of generating improved ultrasound time-sequence image data in an ultrasonic imaging system that employs multiple imaging modes sequentially over time, such as B-mode, Doppler, and color Doppler modes. Aspects of the present disclosure have the technical effect of using degraded image data (e.g., degraded Doppler image data) to predict a patient's blood flow during periods in which no image data (e.g., no Doppler image data) was obtained.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be standalone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical, and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising", "including", or "having" an element or a plurality of elements having a particular property may include additional elements not having that property.

Also as used herein, the term "image" broadly refers to both viewable images and data representing a viewable image (image data). However, many embodiments generate (or are configured to generate) at least one viewable image. In addition, as used herein, the phrase "image" is used to refer to an ultrasound mode, which can be one-dimensional (1D), two-dimensional (2D), three-dimensional (3D), or four-dimensional (4D), and comprising Brightness mode (B-mode), Motion mode (M-mode), Color Motion mode (CM-mode), Color Flow mode (CF-mode), Pulsed Wave (PW) Doppler, Continuous Wave (CW) Doppler, Contrast Enhanced Ultrasound (CEUS), and/or sub-modes of B-mode and/or CF-mode such as Harmonic Imaging, Shear Wave Elasticity Imaging (SWEI), Strain Elastography, Tissue Velocity Imaging (TVI), Power Doppler Imaging (PDI), B-flow, Micro Vascular Imaging (MVI), Ultrasound-Guided Attenuation Parameter (UGAP), and the like.

Furthermore, the term processor or processing unit, as used herein, refers to any type of processing unit that can carry out the required calculations needed for the various embodiments, such as single or multi-core: CPU, Accelerated Processing Unit (APU), Graphic Processing Unit (GPU), Digital Signal Processor (DSP), Field-Programmable Gate Array (FPGA), Application-Specific Integrated Circuit (ASIC), or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system that is operable to automatically place a medical device in an anatomical structure using a locking mechanism, in accordance with various embodiments. Referring to FIG. 1, there is shown an ultrasound system 100 and a training system 200. The ultrasound system 100 comprises a transmitter 102, an ultrasound probe 104, a transmit beamformer 110, a receiver 118, a receive beamformer 120, analog-to-digital (A/D) converters 122, a radio frequency (RF) processor 124, a RF quadrature (RF/IQ) buffer 126, a user input device 130, a signal processor 132, an image buffer 136, a display system 134, and an archive 138.

The transmitter 102 may comprise suitable logic, circuitry, interfaces, and/or code that may be operable to drive an ultrasound probe 104. The ultrasound probe 104 may be a linear, convex, intracavitary, or phased array transducer. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. The group of transmit transducer elements 106 may emit ultrasonic signals through oil and a probe cap and into a target. In a representative embodiment, the ultrasound probe 104 may be operable to acquire ultrasound image data covering at least a substantial portion of an anatomy, such as a heart, an ovary, or any suitable anatomical structure. In an exemplary embodiment, the ultrasound probe 104 may be operated in a volume acquisition mode, where the transducer assembly of the ultrasound probe 104 acquires a plurality of parallel 2D ultrasound slices forming an ultrasound volume.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, and interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces, and/or code that may be operable to demodulate the digital signals output by the plurality of A/D converters 122. In accordance with an embodiment, the RF processor 124 may comprise a complex demodulator (not shown) that is operable to demodulate the digital signals to form me/Q data pairs that are representative of the corresponding echo signals. The RF or I/Q signal data may then be communicated to an RF/IQ buffer 126. The RF/IQ buffer 126 may comprise suitable logic, circuitry, interfaces, and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, select target structures for acquisition of images, input and/or select a region of interest, modify a region of interest, select regions of interest used to acquire images, a focused/zoomed volume, and the like. In an exemplary embodiment, the user input device 130 may be operable to configure, manage, and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera, and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (e.g., summed IQ signal) for generating ultrasound images for presentation on a display system 134. The signal processor 132 is operable to perform one or more processing operations according to a plurality of ultrasound modalities (such as B-mode, Doppler, and color Doppler modalities) on the acquired ultrasound scan data. In an exemplary embodiment, the signal processor 132 may be operable to perform display processing and/or control processing, among other things. Acquired ultrasound scan data, such as a sequence of image data corresponding to a blood-flow in a region of the patient's anatomy, may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise a sequential image acquisition processor 140, a sequential image generator processor 150, and a sequential image discriminator processor 160. The signal processor 132 may be capable of receiving input information from a user input device 130 and/or archive 138, generating an output displayable by a display system 134, and manipulating the output in response to input information from a user input device 130, among other things. The signal processor 132, a sequential image acquisition processor 140, and a sequential image generator processor 150 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 per second but may be lower or higher. As used herein, a "time" or "period of time" may correspond to one or more frames. The acquired ultrasound scan data may be displayed on the display system 134 at a display-rate that can be the same as the frame rate, or slower or faster. A sequence of images (for example of a patient's blood flow) may be displayed simultaneously. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a sequential image acquisition processor 140 that comprises suitable logic, circuitry, interfaces, and/or code that may be operable to use an ultrasound probe 104 to obtain sequential ultrasound image data. In an exemplary embodiment, the sequential image acquisition processor 140 may be configured to capture a sequence of ultrasound images at a target location of the patient's anatomy, such as blood-flow in a particular region of interest of the patient's cardiovascular system. For example, the sequential image acquisition processor 140 may be configured to receive a user input selecting a region of interest prior to performing an ultrasound image acquisition and analyzing the ultrasound image data and/or volume of the ultrasound image acquisition to obtain a sequence of images over time, such as a sequence of images of a patient's blood-flow.

Figure 2:
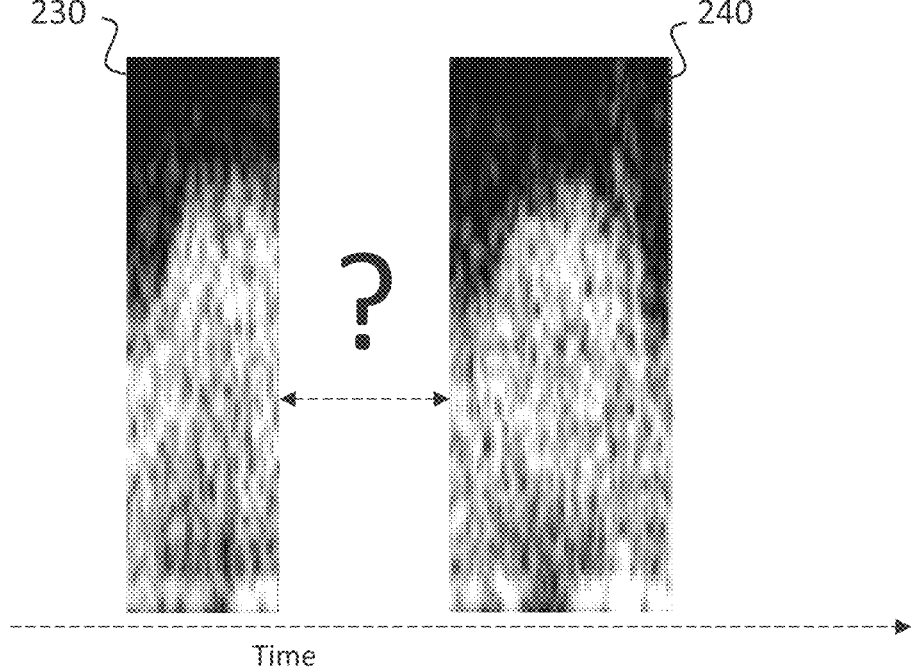
FIG. 2 is an illustration of an incomplete sequence of image data, in which no image data has been acquired at a particular time.

FIG. 2 is an exemplary incomplete sequence of ultrasonic image data. The image data may be Doppler image data, but other types of image data are possible. The image data may be of a patient's blood-flow in a region of interest, and may be obtained by ultrasound system 100. As shown, two sets of image data 230, 240 are obtained at two different times. However, no image data is obtained for a particular period of time between the sets of image data 230, 240. There may be no image data, for example, when ultrasound system 100 switches between modes over time. According to one technique, ultrasound system 100 images a patient using multiple modes over time. One such example is an ultrasound system 100 obtaining Doppler images and B-mode images in an alternating sequence-Doppler, B-mode, Doppler, B-mode, etc. During the time that ultrasound system 100 is obtaining B-mode images, ultrasound system 100 may not be obtaining Doppler images. Therefore, there may be a gap in a sequence of Doppler image data, such as the one shown in FIG. 2. As another example, there may be a gap in Doppler image data when ultrasound system is acquiring color Doppler image data. As another example, image data from a particular time may be ignored or removed for any given reason. In such a circumstance, there may also be a gap.

Referring again to FIG. 1, the sequential image acquisition processor 140 may be configured to gather ultrasound image data as the ultrasound probe 104 is glided across a region of interest, an anatomical structure, tissues, and/or fluids contained therein (such as blood flowing through a region of interest of a patient's cardiovascular system). As the ultrasound probe 104 is glided across such a region, the sequential image acquisition processor 140 gathers ultrasound images and aligns them in a temporal sequence (e.g., left to right), where the first image acquired is the first in the sequence, the second image acquired is the second in the sequence, etc. For example, the sequential image acquisition processor 140 may produce the images shown in FIG. 2. As the ultrasound probe 104 is glided across the region of interest, as mentioned, the sequential ultrasound images may have a gap for durations when no image data was acquired, or undesired image data was acquired.

The sequential ultrasound image data with the gap(s) may be provided by the sequential image acquisition processor 140 to the sequential image generator processor 150. Additionally and/or alternatively, the generated images may be stored at archive 138 and/or any suitable computer readable medium, and the sequential image generator processor 150 may obtain the sequential ultrasound image data from the archive 138 and/or any suitable computer readable medium. In some examples, the sequential image acquisition processor 140 may also be used to generate reference sequential ultrasound image data to be stored in an archive 138, training database 220, and/or any suitable computer readable medium.

The sequential image generator processor 150 may comprise suitable logic, circuitry, interfaces, and/or code that may be operable to obtain the acquired sequential ultrasound image data from the sequential image acquisition processor 140 and/or from the archive 138, training database 220, and/or any suitable computer readable medium. For example, the sequential image generator processor 150 may be configured to receive from the sequential image acquisition processor 140, or retrieve from the archive 138 and/or training database 220, and/or any suitable data storage medium, the acquired sequential ultrasound image with the gap(s).

The sequential image generator processor 150 may receive sequential image data, where the gap(s) have been filled with degraded image data (hereinafter, partially degraded sequential image data). The degraded image data may be generated by mixing noise with the image data obtained before (e.g., immediately before) the gap period. The degraded image data may then be inserted into the gap(s). The partially degraded sequential image data may be obtained by sequential image generator processor 150 from an archive 138, a training database 220, and/or any suitable data storage medium.

Referring to FIG. 1, the sequential image generator processor 150 may comprise suitable logic, circuitry, interfaces, and/or code that may be configured to obtain as input partially degraded sequential ultrasound image data and learn probability distributions in order to produce sample sequential ultrasound image data. For example, the sequential image generator processor 150 may obtain partially degraded sequential image data from the sequential image acquisition processor 140, an archive 138, and/or any other suitable computer readable medium. The sequential image generator processor 150 generates sample sequential ultrasound image data that may appear to be real from the partially degraded sequential image data, which may then be provided to the sequential image discriminator processor 160. Additionally or alternatively, the sample sequential image data may be stored in an archive 138, training database 220, and/or any other suitable computer readable medium, and the sequential image discriminator processor 160 may retrieve the sample sequential ultrasound images from the archive 138, training database 220, and/or any other suitable computer readable medium.

Still referring to FIG. 1, the sequential image discriminator processor 160 may obtain as input, reference sequential ultrasound image data from the sequential image generator processor 150, a training database 220, an archive 138, and/or any other suitable computer readable medium. The sequential image discriminator processor 160 may also be configured to obtain sample sequential ultrasound images from the sequential image generator processor 150 and use the sample sequential ultrasound images to learn to distinguish between the reference images and sample images. The sequential image generator processor 150 may also be operable to obtain reference sequential ultrasound image data from a training database 220, from an archive 138, and/or from any suitable data storage medium.

The reference sequential ultrasound image data may be sequential image data without gaps. The reference sequential ultrasound image data may be previously acquired from a patient, or from a phantom device that simulates fluid flow. Reference sequential ultrasound image data may be acquired under a variety of circumstances and/or conditions. For example, reference sequential ultrasound image data may be acquired at different regions of interest, different blood pressures, different blood speeds, different inner diameters corresponding to different regions of interest, different blood composition, different viscosities, and/or the like. Training may use some or all of such reference sequential ultrasound image data. The reference sequential ultrasound image data may be stored in a training database 220, an archive 138, and/or any suitable data storage medium.

Figure 3:
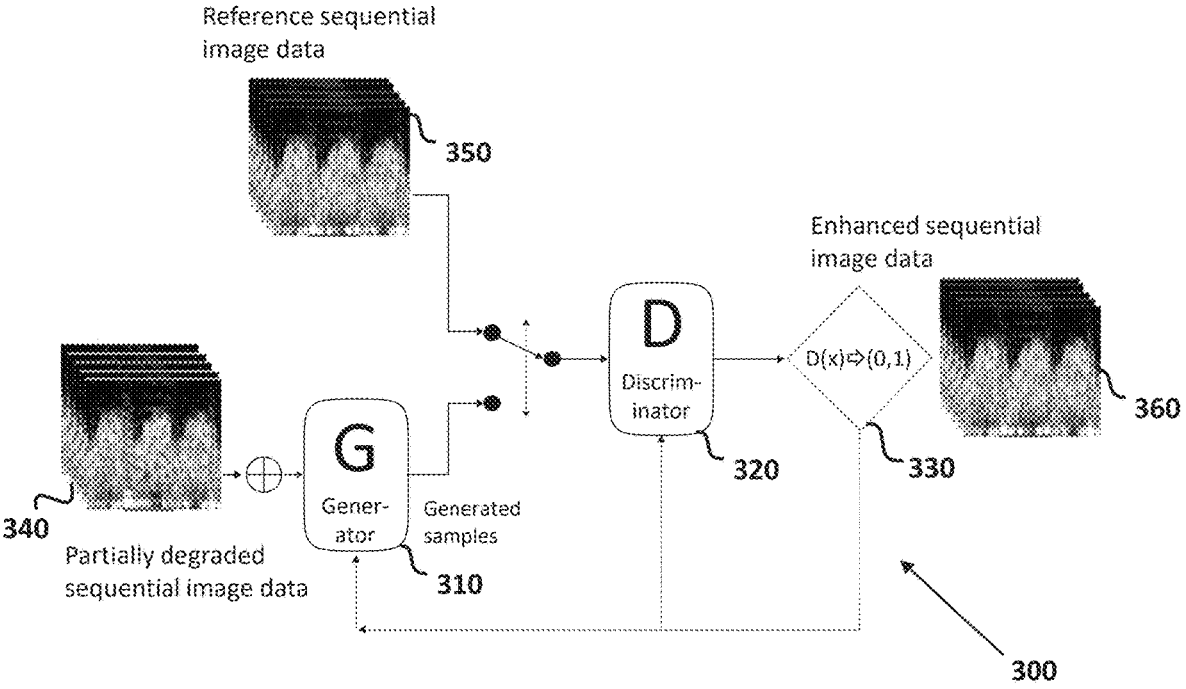
FIG. 3 is an exemplary flow chart for training a machine learning model to generate enhanced image sequence data in the time domain, in accordance with various embodiments.

In some examples, the machine learning model or technique is a generative adversarial network (GAN) model, and the sequential image generator processor 150 and the sequential image discriminator processor 160 perform training using the GAN model. Turning to FIG. 3, generator 310 may be implemented, at least partially, by sequential image generator processor 150. Further, discriminator 320 may be implemented, at least partially, by sequential image discriminator processor 160. The generator 310 may be configured to generate sample sequential ultrasound image data by mapping the partially degraded ultrasound image data to a latent space to learn a probability distribution that the generator 310 may use to generate sample sequential ultrasound images that may appear to be real. At least that is an object of the generator 310—to generate sample sequential ultrasound image data that appears to be real from the partially degraded sequential ultrasound image data.

The objective of the generator 310 may be to learn a distribution $p_\theta(x)$, that approximates a distribution $p_r(x)$ of the reference sequential ultrasonic image data. The generator 310 may generate sample sequential ultrasonic image data having a probability density function $p_G(x)$ that substantially equals the probability density function $p_r(x)$ of the reference sequential ultrasonic image data. The differential function $p_\theta(x)$ may be learned by generator 310, such that $p_\theta(x)>0$ and $\int_x p_\theta(x)dx=1$ and optimize through maximum likelihood. Additionally, or alternatively, generator 310 may learn the differential transformation function $q_\theta(z)$ of $p_\theta(x)$ and optimize through maximum likelihood where z is the existing common distribution such as uniform or Gaussian distribution, as non-limiting examples.

The discriminator 320 may receive the sample sequential ultrasound image data from the generator 310, and may also receive the reference sequential ultrasound image data as inputs. The discriminator 320 may learn to distinguish these two inputs. The discriminator 320 may classify the images as real or generated (from the generator 310) by outputting a value $D(x)$ 330. In some examples, the value is binary (e.g., "0" or "1"). The discriminator 320 may recognize the data from the real data distribution $p_r(x)$, where the function D indicates the estimated probability of data points $x_i \in R^n$. In the case of binary classification, if the estimated probability $D(x_i):\rightarrow R^n[0,1]$ is the positive class $p_i$ and $1-D(x_i):\rightarrow R[0,1]$ is the negative class $q_i$, the cross entropy distribution between $p_i$ and $q_i$ is, $$L(p, q) = -\sum_i^n p_i \log q_i.$$

For a given point $x_i$ and corresponding label $y_i$, the data distribution $x_i$ can be from the real data $x_i \sim p_r(x)$ or the generator data $x_i \sim p_g(z)$. The generator 310 and the discriminator 320 may have an adversarial relationship in which the generator 310 produces false generated image data and the discriminator 320 learns to distinguish between real image data an generated image data. Considering half of the data from the generator 310 and the discriminator as real and generated, the generator 310 and discriminator 320 may contend with each other in a min-max game to minimize the loss function.

$D(x)$ 330 may be provided as feedback to the discriminator 320 and the generator 310. Additionally and/or alternatively, one or more cost and/or loss functions may be used to provide feedback to the generator 310 and the discriminator 320.

As an example, the loss function may be as follows:

$$\min_G \max_D L((x_i, y_i)_{i=1}^n, D) =$$

$$-\frac{1}{2}E_{x \sim p_r(x)}\log D(x) - \frac{1}{2}E_{z \sim p_r(z)}\log[1 - D(G(z))] + \lambda\Psi$$

$$\min_G \max_D L(G, D) = -\frac{1}{2}E_{x \sim p_r(x)}\log D(x) - \frac{1}{2}E_{z \sim p_r(z)}\log[1 - D(G(z))] + \lambda\Psi$$

$$\text{where } \lambda\Psi = E_{x \sim p_r(x^\sim)}\left[\left(\|\nabla_{x^\sim}\|^2 - 1\right)^2\right]$$

to address or overcome the gradient vanish effect.

By competing and receiving feedback, the generator 310 may generate images that resemble real ultrasound images, and the discriminator becomes more adept at distinguishing between real ultrasound images and generated ultrasound images. The objective is for the generated images from the generator 310 to generate ultrasound images that resemble real ultrasound images, at which point the discriminator 320 may also be unable to distinguish between real and generated ultrasound images and training may be considered complete.

Once the training of the generator 310 and the discriminator 320 using the GAN model is complete, the generator 310 may generate enhanced image data, such as enhanced Doppler image data. The image data that fills the gaps may be inferred image data (e.g., inferred Doppler image data), and may be inferred by the trained generator 310 after the generator 310 receives degraded image data (e.g., image data included in partially degraded sequential image data, such as degraded Doppler image data).

Figure 4:
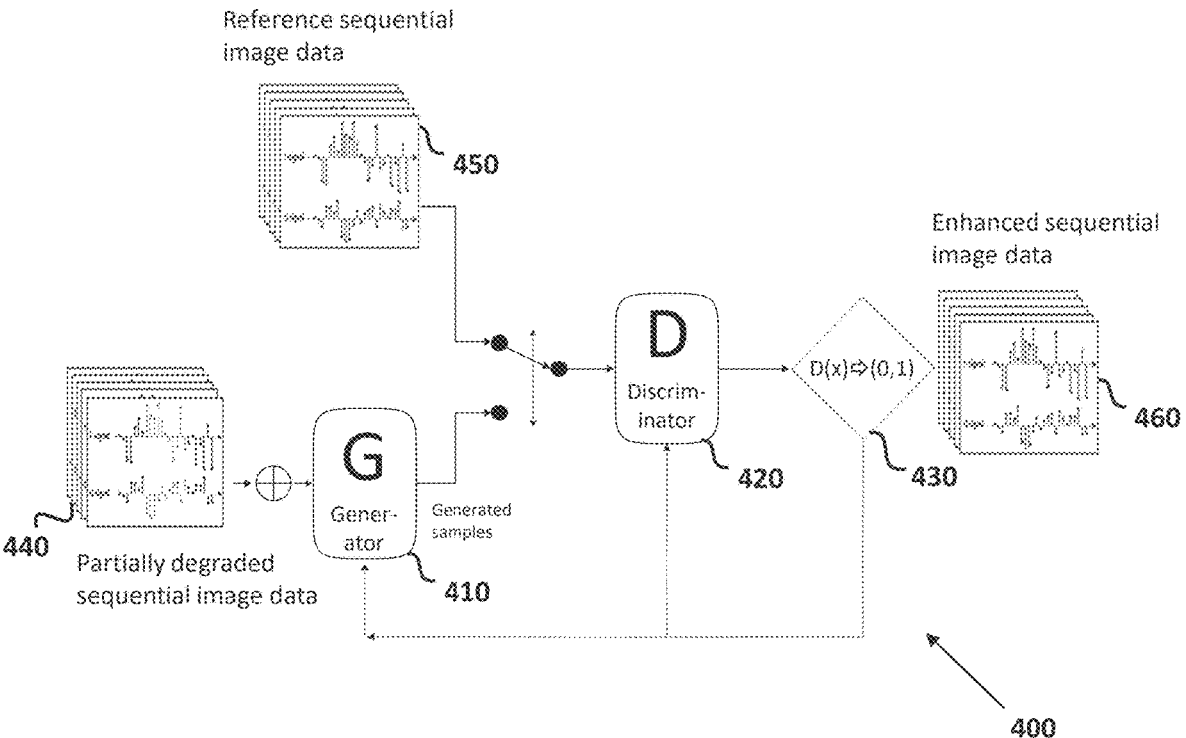
FIG. 4 is an exemplary flow chart for training a machine learning model to generate enhanced image sequence data in the frequency domain, in accordance with various embodiments.

FIG. 3 shows the input image data in the time domain. The input image data may be presented as I and Q components. FIG. 4 may be similar to FIG. 3, except that the processed image data may be in the frequency domain.

Generator 410 may be similar to generator 310, except that generator 410 performs processing on frequency domain data, whereas generator 310 performs processing on time domain data. Discriminator 420 may be similar to discriminator 320, except that discriminator 420 performs processing on frequency domain data, whereas discriminator 320 performs processing on time domain data. Element 430 may be similar to element 330, except that element 430 relates to frequency domain data and element 330 relates to time domain data. Partially degraded sequential image data 440 may be similar to partially degraded sequential image data 340, except that the former is in the frequency domain and the latter is in the time domain. Reference sequential image data 450 may be similar to reference sequential image data 350, except that the former is in the frequency domain and the latter is in the time domain. Enhanced sequential image data 460 may be similar to enhanced sequential image data 360, except that the former is in the frequency domain and the latter is in the time domain.

Referring again to FIG. 1, the display system 134 may be any device capable of communicating visual information to a user. For example, a display system 134 may include a liquid crystal display, a light emitting diode display, and/or any suitable display or displays. The display system 134 can be operable to present 2D ultrasound images, 2D sequential ultrasound images, biplane ultrasound images, biplane ultrasound slices extracted from 3D/4D volumes, rendered 3D/4D volumes, selectable target structures, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores 2D ultrasound images, 2D sequential ultrasound images, biplane ultrasound images, biplane ultrasound slices extracted from 3D/4D volumes, rendered 3D/4D volumes, instructions for acquiring ultrasound image data, instructions for producing sequential ultrasound images, instructions for generating sample sequential ultrasound images, instructions for classifying images as generated or real, instructions for providing feedback based on the classifying of images, instructions for determining that an objective function has been reached, instructions for generating an enhanced sequential ultrasound image, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Still referring to FIG. 1, the training system 200 may comprise a training engine 210 and a training database 220.

The training engine 210 may comprise suitable logic, circuitry, interfaces and/or code that may be operable to train the neurons of the deep neural network(s) (e.g., artificial intelligence model(s)) inferenced (i.e., deployed) by the sequential image acquisition processor 140, the sequential image generator processor 150, and/or the sequential image generator processor 160. For example, the artificial intelligence model inferenced by the sequential image generator processor 150 and/or the sequential image discriminator processor 160 may be trained to automatically acquire an ultrasound image and/or volume using database(s) 220 of classified ultrasound images (e.g., including sequential image data) and/or volumes of anatomical structures. As another example, the artificial intelligence model inferenced by the sequential image acquisition processor 140 may be trained to automatically identify target structures, surrounding structures, target structure shapes, major/minor axes of target structures, and the like depicted in an ultrasound volume using database(s) 220 of classified ultrasound volumes of possible target structures. As another example, classifications may correspond to one or more aspects or parameters of blood flow, as described above.

In various embodiments, the databases 220 of training images may be a Picture Archiving and Communication System (PACS), or any suitable data storage medium. In certain embodiments, the training engine 210 and/or training image databases 220 may be remote system(s) communicatively coupled via a wired or wireless connection to the ultrasound system 100 as shown in FIG. 1. Additionally and/or alternatively, components or all of the training system 200 may be integrated with the ultrasound system 100 in various forms. In some examples, the training image databases may include reference sequential ultrasound images of anatomical structures and/or tissues. In some examples, the reference sequential ultrasound images may be generated by the sequential image acquisition processor 140 and provided to the training image databases 220.

FIG. 5 is a flow chart 500 illustrating exemplary steps 510-580 that may be utilized for training a machine-learning model for enhancing sequential ultrasound images, in accordance with various embodiments. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 510, a signal processor 132 of the ultrasound system 100 may be configured to initiate training to enhance sequential ultrasound images. For example, at step 520, a sequential image discrimination processor 160 may be configured to receive reference sequential ultrasonic image data, for example, from sequential image acquisition processor 140, archive 138, training database 220, and/or other suitable memory. The reference sequential ultrasonic image data may be generated in accordance with the techniques described herein.

At step 530, the sequential image generator processor 150 may receive degraded sequential image data, such as partially degraded sequential image data. The partially degraded sequential image data may include real components at certain times and degraded image data at times between the real components. The partially degraded sequential image data may include alternating sets of real image data with sets of degraded image data. The partially degraded sequential image data may have only one set of real image data at a first time and a set of degraded image data at a second time. The real image data may be provided by the sequential image acquisition processor 140, archive 138, training database 220, and/or other suitable memory. The degraded image data may be image data mixed with noise (e.g., random noise). The image data used to make degraded image data may be obtained from a period of time before the gap (e.g., immediately before the gap). An example of such image data is image data 230 in FIG. 2. The duration of image data may be substantially the same duration as the duration of the gap.

At step 540, the signal processor 132 may be configured to generate sample sequential ultrasound image using the degraded (and/or partially degraded) sequential ultrasound image data. For example, the sequential ultrasound image generator processor 150 may be configured to map the sample sequential ultrasound images to a latent space and to learn a probability distribution that the sequential image generator processor 150 may use to generate sample sequential ultrasound images. The sequential image generator processor 150 may provide the sample sequential ultrasound images to the sequential image discriminator processor 160.

At step 550, the signal processor 132 may be configured to discriminate or classify the sample sequential ultrasound images as real or generated. For example, the sequential image discriminator processor 160 may receive the sample sequential ultrasound images from the sequential image generator processor 150 and reference sequential ultrasound images as input. The sequential image discriminator processor 160 may classify images received as real or generated.

At step 560, the signal processor 132 may be configured to use the results of the classification in order to provide feedback to the sequential image generator processor 150 and the sequential image discriminator processor 160. For example, the sequential image discriminator processor 160 may classify images received as real or generated by outputting a value D(x). In some examples, the value is a binary value (e.g., "0" or "1"). D(x) may be provided as feedback to the sequential image discriminator processor 160 and to the sequential image generator processor 150. Additionally and/or alternatively, one or more cost and/or loss functions may be used to provide feedback to the sequential image generator processor 150 and to the sequential image discriminator processor 160.

At step 570, the signal processor 132 may be configured to repeat steps 540-560 until the objective function is achieved. For example, the sequential image generator processor 150 and the sequential image discriminator processor 160 may have an adversarial relationship in which the sequential image generator processor 150 produces false/generated images and the sequential image discriminator processor 160 learns to distinguish between real sequential ultrasound images and generated sequential ultrasound images. By competing and receiving feedback, the sequential image generator processor 150 may generate sequential ultrasound images that resemble real sequential ultrasound images, and the sequential image discriminator processor 160 becomes more adept at distinguishing between real sequential ultrasound images and generated sequential ultrasound images. The objective is for the generated sequential ultrasound images from the sequential image generator processor 150 to resemble real ultrasound images, and/or for the sequential image discriminator processor 160 to be unable to distinguish between real and generated ultrasound images. Once the objective function is achieved, training is complete at step 580.

FIG. 6 is a flow chart 600 illustrating exemplary steps 610-630 that may be utilized to enhance sequential ultrasound images using deep learning, in accordance with various embodiments. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 610, the trained machine-learning model may receive incomplete sequential image data, such as the data shown in FIG. 2. The data may be gathered by a signal processor 132 as the ultrasound probe 104 is glided across a region of interest of an anatomical structure and/or tissues and/or fluids such as blood contained therein. As the ultrasound probe 104 is glided across the region of interest, the sequential image acquisition processor 140 gathers incomplete sequential ultrasound image data. The image data may be incomplete because the image data is only for one mode (e.g., Doppler mode), and the ultrasound system 100 may switch to other modes (e.g., B-mode or color Doppler mode) during the gap periods.

At step 620, image data for the gaps may be generated. This data may be degraded image data. This data may be generated by mixing noise (e.g., random noise) with image data obtained before the gap (e.g., immediately before the gap). The generated gap data and the incomplete data received at step 610 may be combined. The different data may be combined by the signal processor 132, or may be combined before being received by the signal processor 132 (e.g., received by the sequential image generator processor 150).

At step 630, enhanced sequential image data may be generated by the signal processor 132. The enhanced sequential image data may be generated by sequential image generator processor 150 based on prior training and the combination of the incomplete data and the image data placed in the gaps of the incomplete data. For example, the sequential image generator processor 150 that has been trained using, for example the method of FIG. 6, may receive the incomplete image data and/or the added image data (e.g., the degraded image data) from the sequential image acquisition processor 140 and/or other sources, and may generate an enhanced sequential ultrasound image. The enhanced sequential ultrasound image data generated by the signal processor 132 may be similar to the incomplete sequential image data, except the enhanced sequential image data is complete and does not include gaps.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for enhancing sequential ultrasound images using deep learning.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

The invention claimed is:

1. A method for enhancing sequential ultrasound image data in an ultrasound system, comprising:
  acquiring by an ultrasound probe of the ultrasound system, first image data during a first period of time and third image data during a third period of time subsequent to the first period of time; and
  inferring inferred image data corresponding to a second period of time, wherein the second period of time is intermediate the first period of time and the third period of time, wherein the inferred image data is inferred by:
  inputting, into a trained machine-learning model, degraded image data; and
  generating, by the trained machine-learning model, the inferred image data,
  wherein the degraded image data is obtained by mixing noise with the first image data.

2. The method of claim 1, wherein the first image data, the third image data, and the inferred image data include Doppler image data.

3. The method of claim 2, wherein the inferred image data includes time domain data.

4. The method of claim 2, wherein the inferred image data includes frequency domain data.

5. The method of claim 2, further comprising acquiring B-mode data during the second period of time.

6. The method of claim 2, wherein the trained machine-learning trained model comprises a generative adversarial network (GAN) model.

7. The method of claim 6, wherein the GAN model includes a generator and a discriminator, and further comprising training the GAN model by:
  inputting the degraded image data into the generator;
  outputting, by the generator, samples corresponding to the degraded image data to the discriminator;
  inputting reference image data into the discriminator; and
  discriminating with the discriminator between the degraded image data and the reference image data with the discriminator according to at least one function.

8. The method of claim 7, wherein the samples comprise a probability density function of real samples of the degraded image data.

9. The method of claim 7, wherein said discriminating with the discriminator further comprises minimizing a loss function.

10. The method of claim 7, wherein the reference image data is obtained from imaging of a phantom device.

11. The method of claim 7, wherein the degraded image data is generated by mixing noise with the first image data.

12. A system for enhancing sequential ultrasound image data, comprising:
  an ultrasound probe configured to obtain first image data during a first period of time and third image data during a third period of time subsequent to the first period of time; and
  a processor configured to infer inferred image data corresponding to a second period of time, wherein the second period of time is intermediate the first period of time and the third period of time,
  wherein the inferred image data is inferred by: inputting, into a trained machine-learning model, degraded image data; and generating, by the trained machine-learning model, the inferred image data,
  wherein the processor is further configured to generate the degraded image data by mixing noise with the first image data.

13. The system of claim 12, wherein the first image data, the third image data, the inferred image data include Doppler image data.

14. The system of claim 13, wherein the ultrasound probe is further configured to acquire B-mode data during the second period of time.

15. The system of claim 12, wherein the trained machine-learning trained model comprises a generative adversarial network (GAN) model.

16. The system of claim 15, wherein the processor is further configured to implement the GAN model using a generator and a discriminator, and wherein the processor is further configured to train the GAN model by:
  inputting the degraded image data into the generator;
  outputting, by the generator, samples corresponding to the degraded image data to the discriminator;
  inputting reference image data into the discriminator; and
  discriminating with the discriminator between the degraded image data and the reference image data with the discriminator according to at least one function.

17. The system of claim 16, wherein the degraded image data is generated by mixing noise with the first image data.

* * * * *